United States Patent [19]

Clarke

[11] 4,172,666

[45] Oct. 30, 1979

[54] INSPECTION APPARATUS

[75] Inventor: Graham M. Clarke, Edinburgh, Scotland

[73] Assignee: Ferranti Limited, Hollinwood, England

[21] Appl. No.: 853,462

[22] Filed: Nov. 21, 1977

[30] Foreign Application Priority Data

Dec. 1, 1976 [GB] United Kingdom ............... 50184/76

[51] Int. Cl.$^2$ .......................................... G01N 21/16
[52] U.S. Cl. .................................... 356/431; 250/563; 356/446
[58] Field of Search ............... 356/200, 209, 210, 237, 356/431, 445, 446, 237; 250/563

[56] References Cited

U.S. PATENT DOCUMENTS

| 3,176,306 | 3/1965 | Burns ................................... 356/237 |
| 3,922,093 | 11/1975 | Dandliker et al. ................... 356/237 |
| 3,984,189 | 10/1976 | Seki et al. ............................ 356/200 |

Primary Examiner—John K. Corbin
Assistant Examiner—R. A. Rosenberger
Attorney, Agent, or Firm—Cameron, Kerkam, Sutton, Stowell & Stowell

[57] ABSTRACT

To distinguish between different types of fault detected by laser scanning of a moving web two or more detectors are arranged to collect light reflected in different ranges of angles in direction of web motion. By combining outputs of these in a logical way representing increases or decreases in the sums and differences of the signals they produce, the faults can be classified as absorbing, scattering, or their opposites, or deflecting.

3 Claims, 14 Drawing Figures

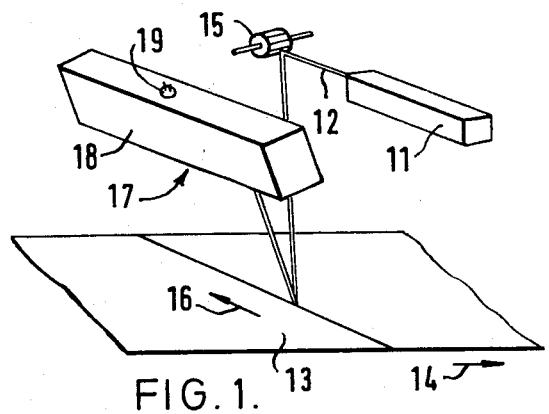
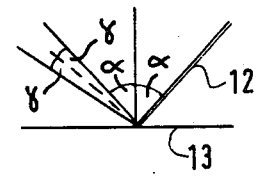
FIG. 1.   FIG. 2.
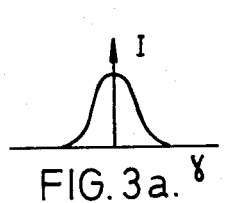 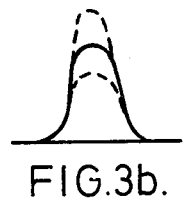 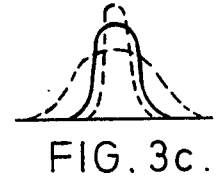 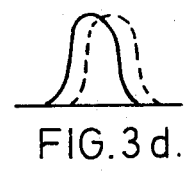
FIG. 3a.   FIG. 3b.   FIG. 3c.   FIG. 3d.
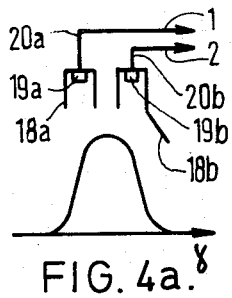
FIG. 4a.
|   | 1 | 2 | 1+2 | 1−2 | 48 | 50 | 52 |
|---|---|---|-----|-----|----|----|----|
| A | B | B | B | 0 | 1 | | |
| S− | B | B | B | 0 | 1 | | |
| D | W/B | B/W | W | W/B | | 1 | |
| S | W | W | W | 0 | | | 1 |
| A− | W | W | W | 0 | | | 1 |
FIG. 4b.
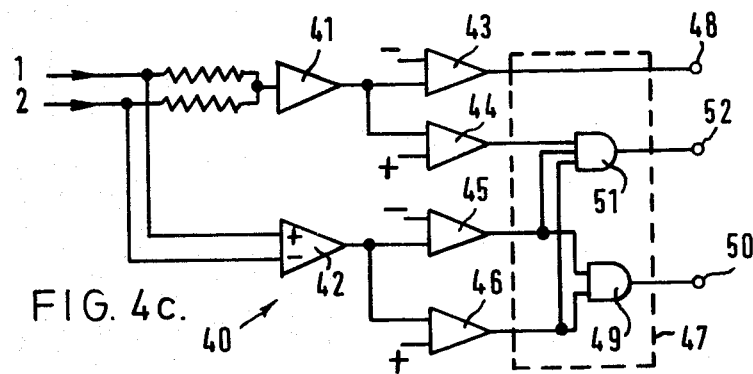
FIG. 4c.

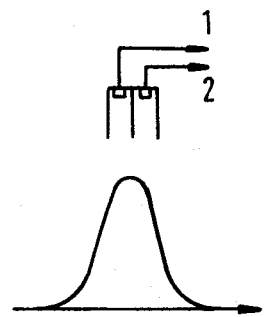
FIG. 5a.
| | 1 | 2 | 1+2 | 1-2 | 48 | 50 | 52 |
|---|---|---|---|---|---|---|---|
| A | B | B | B | 0 | 1 | | |
| S- | U | U | W | 0 | | | 1 |
| D | W/B | B/W | U | W/B | | 1 | |
| S | U | U | B | 0 | 1 | | |
| A- | W | W | W | 0 | | | 1 |
FIG. 5b.
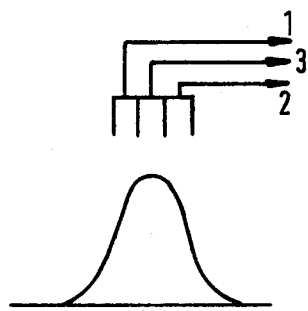
FIG. 6a.
| | 1 | 2 | 3 | 1+2 | 1-2 | 1+2+3 | 72 | 77 | 78 | 83 | 84 |
|---|---|---|---|---|---|---|---|---|---|---|---|
| A | B | B | B | B | 0 | B | | 1 | | | |
| S- | B | B | W | B | 0 | U | | | | 1 | |
| D | W/B | B/W | B | W | W/B | U | 1 | | | | |
| S | W | W | B | W | 0 | U | | | | | 1 |
| A- | W | W | W | W | 0 | W | | | 1 | | |
FIG. 6b.
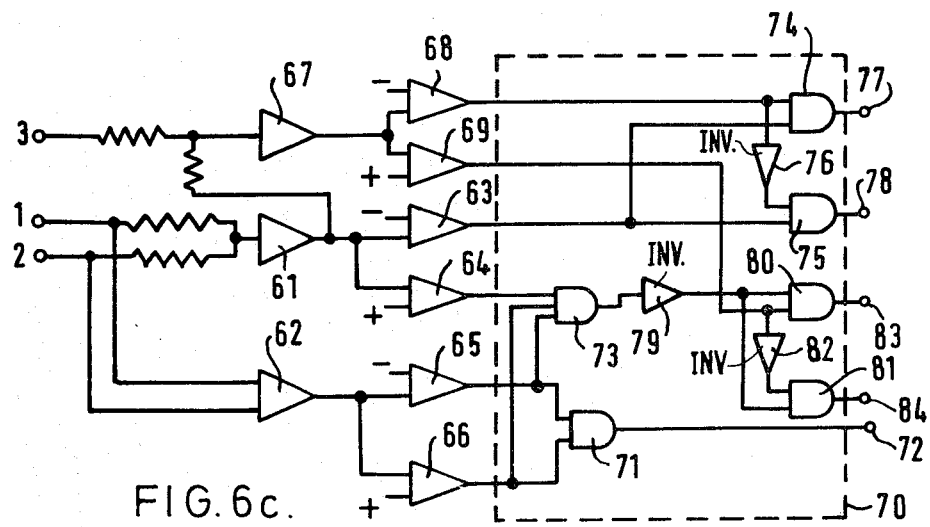
FIG. 6c.

INSPECTION APPARATUS

This invention relates to optical inspection apparatus.

Optical inspection apparatus is known in which light, confined to a narrow beam, is scanned repetitively over an object or web moving past the apparatus transversely to the direction of scan of the beam. Light reflected from, or transmitted by, the web is collected by a suitably located receiver containing a photodetector. The photodetector signal for a fault-free material remains substantially constant throughout the scan (subject to any predictable variations due to the optical characteristics of the system) so that any change in the level of light detected is indicative of a fault in the web. The sensitivity of the apparatus is maximised by making the area of the beam striking the web of the same magnitude as the faults to be detected so that the light emanating from the web is affected to a much greater extent by the fault. Such optical apparatus will hereafter be referred to as "of the type described".

Such apparatus is adequate when any fault occurring is of significance or when it is required to know the total number of faults, but is does not provide information on the optical characteristics of a fault in respect of the effect it has on light incident on it, which characteristics may determine its importance to the inspection operation.

It is an object of the present invention to provide detection means capable of discriminating between classes of faults exhibiting different optical characteristics.

According to the present invention detection means for optical inspection apparatus of the type described and arranged to discriminate between classes of fault exhibiting different optical characteristics comprises a plurality of photodetectors each arranged to receive throughout the scan light emanating from the scanned area over a separate range of angles transversely to the direction of scan and responsive to an increase or decrease in the intensity of the received light to produce a detector signal having a polarity indicative of the sense of said change, signal processing means operable to combine the photodetector signals into sum and difference signals and to separate said sum and difference signals into channels in accordance with their polarities, and gating means operable to control the passage of said sum and difference signals to separate output terminals, the appearance of signals thereat being indicative of the detection of a fault having optical characteristics in at least one, but not all, of the classes.

There may be two detectors, the signal processing means comprising a first amplifier arranged to receive and sum the two detector signals to produce said sum signal, a second amplifier arranged to receive and subtract the two detector signals to produce said difference signal, a first comparator connected to the output of the first amplifier and to a first threshold voltage of one polarity to produce an output only when the sum signal exceeds the amplitude of the threshold voltage and is of said one polarity, a second comparator also connected to the output of the first amplifier and to a second threshold voltage of opposite polarity to provide an output only when the sum signal exceeds the amplitude of the threshold signal in said opposite polarity, a third comparator connected to the output of the second amplifier and to a third threshold voltage of said one polarity to produce an output only when the difference signal exceeds the amplitude of the third threshold voltage in said one polarity and to a fourth threshold voltage of said other polarity to produce an output only when the difference signal exceeds the amplitude of the threshold voltage in said other polarity.

The four threshold voltages may all be of the same amplitude.

The one polarity may be negative with respect to earth and indicative of a reduction in intensity of received light.

The gating means may be operable to connect the sum signal of one polarity directly to a first output terminal, operable to connect the difference signals of both polarities to a second output terminal by way of a first gate, the gate being operable to pass signals to the second output terminal when there is a difference signal of one polarity or the other, and operable to connect the sum signal of the other polarity to a third output terminal by way of a second gate arranged to pass said sum signal only in the absence of a difference signal.

The two detectors may be spaced apart so as to collect only light at angles on each side of the path of that directly reflected, or transmitted, by the object or web, the first output terminal then providing a signal indicative of a fault being either absorbing of light or causing a local sharpening of the distribution of light, the second output terminal providing a signal indicative of a fault causing deflection of the light beam and the third output terminal providing a signal indicative of a fault causing scattering of the light or of a bright fault on a dark background.

Alternatively the two detectors may be located adjacent each other so as to receive light at angles including and closely adjacent to the angle of direct reflection or transmission, the first output terminal providing a signal indicative of a fault causing either absorption or scattering of the light, the second output terminal providing a signal indicative of a fault causing deflection of the light beam and the third output terminal providing a signal indicative of a fault causing either a local sharpening of the distribution of light or of a bright fault on a dark background.

Arrangements described in the above paragraphs are suitable for use where one of alternative interpretations of an output signal is not allowable by virtue of the properties of the material of the object or web being inspected.

There may be three photodetectors located adjacent to each other one of the detectors receiving light directly transmitted or reflected, and the other two symmetrically located one at either side of said one detector, the signal processing means being operable to produce the sum of the three photodetector signals as well as the sum and difference signals from the two symmetrically disposed outer detectors, and including fifth and sixth comparators to separate sum signals of all three detectors of said one or said other polarity, respectively, and the gating means including third and fourth gates arranged to receive directly the signals from the first comparator, and, directly and by way of an inverter, respectively, the signals from the fifth comparator and arranged to pass the respective output terminal signals indicative of a fault causing absorption and of local sharpening of the distribution, and fifth and sixth gates arranged to receive by way of an inverter signals from the second gate and, directly and by way of an inverter, respectively, signals from the sixth comparator, said gates being arranged to pass to respective output terminals signals indicative of a fault causing scattering or a bright fault on a dark background.

The third, fourth, fifth and sixth gates may be NAND gates and the fifth and sixth comparators may be arranged to produce signals of opposite polarity of the first and fourth comparators.

Embodiments of the invention will now be described by way of example with reference to the accompanying drawings, in which:

FIG. 1 is a perspective view of a typical inspection apparatus with which the present invention is concerned, FIG. 2 is an illustration used to explain the effects of reflection from a surface, FIGS. 3a to 3d show distribution curves to illustrate the effects of different types of fault on light reflected from a surface as in FIG. 2, FIG. 4a shows a section through detection apparatus according to the present invention and employing two spaced photodetectors located with respect to an intensity distribution curve of light reflected from a surface being inspected, FIG. 4b is a table showing the relationship between photodetector signals and types of fault, FIG. 4c is a circuit arrangement showing manipulation of the photodetector signals in accordance with the table of FIG. 4b, FIG. 5a shows a section through detection apparatus similar to FIG. 4a but with the photodetectors located to receive light from adjacent parts of the reflected beam, FIG. 5b is a table showing the relationship between photodetector signals and types of faults for the arrangement of FIG. 5a, FIG. 6a shows a section through detection means according to the present invention employing three photodetectors and their location with respect to the reflected beam in terms of the intensity distribution curve, FIG. 6b is a table showing the relationship between photodetector outputs and types of faults for the arrangement of FIG. 6a, and FIG. 6c is a circuit arrangement similar to that of FIG. 4c but providing complete separation of fault types in accordance with the table of FIG. 6b.

Referring to FIG. 1, known optical inspection apparatus comprises a laser 11 which produces a continuous beam 12 of light directed onto a surface 13, moving in the direction of arrow 14, by a rotating multifaceted mirror 15. The mirror is so located that the beam scans the surface in the direction of arrow 16 transversely to the direction of movement of the surface. Light reflected from the surface throughout the scan is collected in a receiver arrangement 17 comprising a detector 19 in an enclosure 18, the enclosure being inclined to the surface in the direction of relative movement to receive reflected light from the surface. The photodetector can be made to produce substantially constant amplitude of signal output throughout the scan for a particular surface, a change in amplitude, either an increase or decrease, being indicative of a surface fault providing an increase or decrease in intensity of received light and causing a positive-going (conveniently called "white") or negative-going (conveniently called "black") photodetector signals, respectively.

Referring to FIG. 2 the beam 12 is incident on a surface 13 at an angle $\alpha$ to the normal to the surface and is reflected at angles $\alpha + \gamma$ as a result of surface properties and imperfections.

FIG. 3a shows a typical distribution curve for reflected light comprising the relationship between intensity I and angle $\gamma$. The receiver enclosure 18 is arranged to receive light reflected mainly at the angle $\alpha$ but the aperture is made wide enough to receive light at angle $\gamma$ sufficient to ensure that a maximum light falls on the photodetector.

The photodetector detects a fault by a change in the intensity of light received, as a result of a change in the distribution curve, but is unable to distinguish the form of the change and further identify the fault.

FIGS. 3b, 3c and 3d show in full lines typical intensity distribution curves for light reflected from a surface and superimposed thereon the shapes assumed by the curves as a result of the light striking different types of faults, which fall into five main classes. FIG. 3b shows by the broken line the distribution curve resulting from an absorbing fault (A) which causes a reduction in the overall amount of light reflected. The chain dashed lines show an increase in the amount of light reflected, as from a bright fault on a dark background. As this gives the opposite effect to an absorbing fault it is classed as an A- fault. FIG. 3c shows by broken line the effect of a light scattering fault (S) which causes a broadening of the curve and the chain dashed line shows the effect of a light "concentrating" fault S- in which there is a local sharpening of the reflected beam. FIG. 3d shows by broken line the effect of a light deflecting fault (D) which causes a temporary shift in the axis of the distribution curve. This shift is temporary in either direction followed by a return to its normal position.

In one embodiment of the present invention the detection means, as shown in FIG. 4a, comprises two enclosures 18a and 18b containing a photodetector 19a and 19b providing detector signals on lines 20a and 20b, respectively. For convenience of description the photodetector 19a signal and the channel it occupies are identified as 1 and the photodetector 19b signal and the channel it occupies are identified as 2. FIG. 4a also shows the relationship between the two photodetectors and the angle $\gamma$. Considering the effects of the five classes of fault on the detectors signals, the table of FIG. 4b shows in the two left hand columns the photodetector signals to be expected on the channels 1 and 2, bearing in mind that a B signal denotes a decrease in intensity of received light and W an increase. The effect of a D fault may be of either sense. The next two columns illustrate the signals obtained from combination of signals (1+2) and (1−2), and the circuit arrangement of FIG. 4c shows how the signal combinations may be made.

The signals of channels 1 and 2 are summed in the summing amplifier 41 to give a signal (1+2) and are subtracted in a difference amplifier 42 to give a signal (1−2). The output of amplifier 41 is taken to first and second comparators 43 and 44. The first comparator 43 is also supplied with a negative threshold voltage so as to produce a signal only when the sum (1+2) is negative going, that is B, and the second comparator 44 is supplied with a positive threshold so as to produce a signal only when the sum (1+2) is positive going, that is W. Similarly the difference signal (1−2) is fed to third and fourth comparators 45 and 46 which respond to B and W polarities of signals, respectively. The signals are fed from the comparators to gating means 47. The output of comparator 43 is taken directly to a first output terminal 48. The output of comparators 45 and 46 fed to a first NAND gate 49 which produces an output signal to a second output terminal 50. The output of comparators 45 and 46 and of comparator 44 are also fed to a second NAND gate 51 which produces an output signal to a third output terminal 52.

Consdering operation with reference to the table of FIG. 4b, a signal appearing at the first output terminal 48 will be indicative of a B signal in the sum channel, that is an A or S- fault. A signal appearing at the second output terminal 50 will be indicative of a signal of either polarity in the (1−2) channel, which it will be seen from the table is indicative of a D fault.

The output of comparator 44 is indicative of a W on the sum channel and thus of an S, A- or D fault. The NAND gate 51 inhibits passage of a signal when a difference signal of either polarity occurs thereby preventing an output signal at the third output terminal 52 due to a D fault. Any output signal that does occur is thus due to an S or A- fault. The three right-hand columns of the table show the relationship between the fault types and the appearance of a signal (shown as a 1) at the output terminals.

The circuit, while producing possibly ambiguous results for a surface having any faults, is nevertheless useful for a system in which the surface to be scanned is known to be free of one of the classes of fault leading to an ambiguous result.

A similar arrangement suitable for use with a restricted number of faults may be employed in which the first and third output terminals produce signals indicative of more than one type of fault but in a different combination to the arrangement described above. Referring to FIGS. 5a and 5b, the receiver housings 18a and 18b are located adjacent each other and separated only by a very thin partition corresponding to an angle $\gamma=0$. The receivers have narrow apertures so as to receive light reflected just to either side of the angle of direct reflection. From the table of FIG. 5b it will be seen that the signal of channels 1 and 2 are B for an A fault, W for an A- fault, W and B respectively or B and W, respectively, for a D fault and unchanged U for an S or S-fault. Considering the sum and difference signals (1+2) and (1−2) it will be seen that the first output terminal 48 provides a signal indicative of an A or S fault, that third output terminal 52 provides a signal indicative of an S- or A- fault, and that second output terminal 50 provides a signal indicative of a D fault. With this type of arrangement it may occur that, for a small total aperture, S faults give the same signal of response as A and A- as light can spread outside the total aperture, and as such may not be suitable for measuring S faults even in the absence of A faults showing in the same channel.

A more comprehensive arrangement giving complete classification of the five types of faults is shown in FIG. 6a, and comprises an arrangement of three adjacent enclosures and detectors, a centre detector arranged to receive light directly reflected to produce a photodetector signal on a channel 3, and symmetrically disposed at either side thereof a pair of outer detectors giving signals on channels 1 and 2 as with the arrangement of FIG. 4a. FIG. 6b shows a table of the photodetector signals produced on each channel in response to the appropriate fault and the polarity of signals formed as sum and difference signals for channels 1 and 2 and the sum signal of channels 1, 2, and 3. It will be appreciated that the 1 and 2 signals will be as for the spaced detectors of FIG. 4a and that the 3 signal will be B for A, D and S faults as the light collected decreases, and W for S- and A- as the light collected at the direct angle of reflection increases.

The three detector signals are combined in the form shown in the table, that is (1+2), (1−2) and (1+2+3) by the circuit arrangement of FIG. 6c. The photodetector signals from channels 1 and 2 are summed and subtracted in amplifiers 61 and 62 respectively and the signals (1+2) and (1−2) are separated into B and W channels by first-fourth comparators 63–66. Photodetector signal 3 is summed with the output of amplifier 61 in amplifier 67 to give a signal (1+2+3) which signal is separated into B and W channels by fifth and sixth comparators 68 and 69 respectively.

The outputs of the comparators are fed to output terminals by way of gating means 70.

The outputs of third and fourth comparators 65 and 66 are passed by a first NAND gate 71 (corresponding to the first gate 48 of FIG. 4b) to a second output terminal 72, to produce an output signal indicative of the detection of a D fault. The outputs of comparators 65 and 66 are fed with the output of second comparator 64 to second NAND gate 73 to ensure that no W signal is passed along the W channel when a (1−2) signal is available.

The outputs of the first comparator 63 is fed directly to one input of a two-input third NAND gate 74 and to one input of a two-input fourth NAND gate 75, the second input being from the fifth comparator directly to gate 74 and by way of an inverter 76 to gate 75. The outputs of the gates 74 and 75 are fed to output terminals 77 and 78 respectively. The gating means serves to differentiate between the two possible causes of a B signal in the (1+2) channel by whether a B signal appears on the (1+2+3) channel. Thus the output terminal 77 provides an output signal if an A- fault is detected and terminal 78 provides an output signal of an S fault is detected.

The output of the second comparator 64 is fed by way of the second gate 73 and an inverter 79 to one input of a fifth two-input NAND gate 80 and to one input of a sixth two-input NAND gate 81. The output of the comparator 69 is taken directly to the other input of gate 80 and by way of inverter 82 to the other input of gate 81. The gates feed outputs terminals 83 and 84, respectively, and serve to separate W signals on the (1+2) channel in accordance with whether the (1+2+3) signal is white or not. Thus the output terminal 84 produces a signal upon detection of an S fault and output terminal 83 produces a signal upon detection of an A- fault. The five right-hand columns of the table of FIG. 6b show the relationships between the faults and signals appearing at the circuit output terminals.

It will be understood that the circuit of FIG. 6c is shown in schematic form to avoid clutter but requires in practice to employ standard methods such as pulse stretching or memory storage for resolving factors such a simultaneity of input signals producing logical race problems.

For the appropriate numbers of photodetectors employed in the above described embodiments only two threshold levels, that is, B and W have been shown. Multiple threshold levels may be used in order that mixed responses can be allowed and the arrangement is not restricted to pure signals of each type.

The D faults causing deflection of the reflected beam may be due to different effects, some due to the surface and some due to the effects of the inspection system. Instability of the system machinery, such as surface wobble or machine vibration, gives rise to deflection signals with long term responses with respect to the time of scan. Dents in the surface produce response signals of "medium" duration while surface texture produces "short" duration responses. It will be appreciated that the D output terminal 50 (FIG. 4c) or 72 (FIG. 6c) may be fed to a suitable filter network (not shown) to separate further the D responses by virtue of their duration.

All the above embodiments have been described with reference to reflection from a surface but it will be appreciated that they are equally applicable to light received by way of transmission through a material.

What is claimed is:

1. Detection means for optical inspection apparatus of the type wherein light, confined to a narrow beam, is scanned repetitively over a web moving past the apparatus transversely to the direction of scan of the beam and light reflected from or transmitted by the web is collected by a receiver containing a photodetector which produces signals indicative of changes in the level of light collected caused by faults in the web, said detection means being arranged to discriminate between classes of fault exhibiting different optical characteristics and comprising three photodetectors each arranged to receive throughout the scan light emanating from the scanned area over a separate range of angles transversely to the direction of scan, one of said detectors being located to receive light directly reflected at the specular angle and the other two detectors being spaced apart one on each side of the specular angle, the detectors being responsive to an increase or decrease in the intensity of the received light to produce a detector signal having a polarity indicative of the sense of the change, signal processing means comprising a first amplifier arranged to receive and sum the detector signals of the two outer detectors to produce a sum signal, a second amplifier arranged to receive and subtract said two detector signals to produce a difference signal, a third amplifier associated with the central detector and the first amplifier to provide a signal representing the sum of the three detector signals, a first comparator connected to the output of the first amplifier and to a first threshold voltage of one polarity to produce an output only when the sum signal exceeds the amplitude of the threshold voltage and is of said one polarity, a second comparator also connected to the output of the first amplifier and to a second threshold voltage of opposite polarity to provide an output signal only when the sum signal exceeds the amplitude of the threshold signal of said opposite polarity, a third comparator connected to the output of the second amplifier and to a third threshold voltage of said one polarity to produce an output only when the difference signal exceeds the amplitude of the third threshold signal the threshold voltage of said one polarity, a fourth comparator connected to the output of the second amplifier and to a fourth threshold voltage of said other polarity to produce an output only when the difference signal exceeds the amplitude of the threshold voltage of said other polarity, and fifth and sixth comparators operable to separate sum and difference signals from the third amplifier into signal channels of said one or other polarity respectively, and gating means comprising a first gate operable to connect the difference signals of both polarities to an output terminal when there is a difference signal of one polarity or the other, indicative of a fault causing displacement of the beam, a second gate arranged to receive difference signals and operable to pass the sum signal of the other polarity only in the absence of a difference signal, third and fourth gates arranged to receive directly the signals from the first comparator and directly and by way of an inverter, respectively, the signals from the fifth comparator and arranged to pass to the respective output terminals signals indicative of a fault causing absorption or of local sharpening of the distribution, and fifth and sixth gates arranged to receive by way of an inverter signals from the second gate and, directly and by way of an inverter, respectively, signals from the sixth comparator, said fifth and sixth gates being arranged to pass to respective output terminals signals indicative of a fault causing scattering or a bright fault on a dark background.

2. Detection means as claimed in claim 1 in which the third, fourth, fifth and sixth gates are NAND gates and the fifth and sixth comparators are arranged to produce signals of opposite polarity of those of the first to fourth comparators.

3. Detection means as claimed in claim 1 including filter means connected to receive signals from the second output terminal and operable to direct the signals to different output terminals in accordance with the durations of the signals.

* * * * *